(12) United States Patent
Munn

(10) Patent No.: US 10,953,120 B1
(45) Date of Patent: Mar. 23, 2021

(54) SYSTEM FOR NEUTRALIZING PATHOGENS ON TACTILE SURFACES

(71) Applicant: STERILUMEN, INC., Tarrytown, NY (US)

(72) Inventor: Max Munn, Tarrytown, NY (US)

(73) Assignee: STERILUMEN, INC., Tarrytown, NY (US)

( * ) Notice: Subject to any disclaimer, the term of this patent is extended or adjusted under 35 U.S.C. 154(b) by 0 days.

(21) Appl. No.: 16/983,412

(22) Filed: Aug. 3, 2020

(51) Int. Cl.
*A61L 2/10* (2006.01)
*G07F 19/00* (2006.01)
*A61L 2/24* (2006.01)

(52) U.S. Cl.
CPC .................. *A61L 2/10* (2013.01); *A61L 2/24* (2013.01); *G07F 19/205* (2013.01); *A61L 2202/11* (2013.01); *A61L 2202/14* (2013.01)

(58) Field of Classification Search
USPC .................................................. 250/455.11
See application file for complete search history.

(56) References Cited

U.S. PATENT DOCUMENTS

| | | | | |
|---|---|---|---|---|
| 6,458,331 B1 * | 10/2002 | Roberts | ...................... | A61L 2/10 422/186.3 |
| 7,847,948 B2 * | 12/2010 | Lee | ...................... | G06K 9/0004 356/445 |
| 8,597,569 B2 * | 12/2013 | Gruen | ................... | G06F 1/1601 422/24 |
| 8,598,539 B2 * | 12/2013 | Chuang | ................... | B66B 1/466 250/455.11 |
| 2006/0188389 A1 * | 8/2006 | Levy | ......................... | A61L 2/24 422/24 |
| 2017/0080117 A1 | 3/2017 | Gordon | | |
| 2018/0339075 A1 | 11/2018 | Kennedy et al. | | |

FOREIGN PATENT DOCUMENTS

| | | |
|---|---|---|
| CN | 208552563 | 3/2019 |
| WO | 2016190828 | 12/2016 |
| WO | 2018101943 | 6/2018 |

* cited by examiner

*Primary Examiner* — Phillip A Johnston
(74) *Attorney, Agent, or Firm* — Nolte Lackenbach Siegel; Myron Greenspan

(57) ABSTRACT

A device for neutralizing pathogens on a tactile surface arranged to be touched or contacted by a user's hand includes a housing adapted to be attached to a support surface, such as a wall of an ATM, generally above the tactile surface. A UV light source is provided on the housing arranged to irradiate UV radiation on the tactile surface. A personnel detector is provided for detecting the presence of a person in sufficient proximity to the tactile surface to touch or contact the tactile surface. Control circuitry, preferably in the form of a programmable controller, is provided for normally energizing the UV light source and de-energizing the UV light source upon detection of a user in sufficient proximity to allow a user to touch or contact the tactile surface. A white light source is provided to illuminate the tactile surface when the UV light source is de-energized.

18 Claims, 4 Drawing Sheets

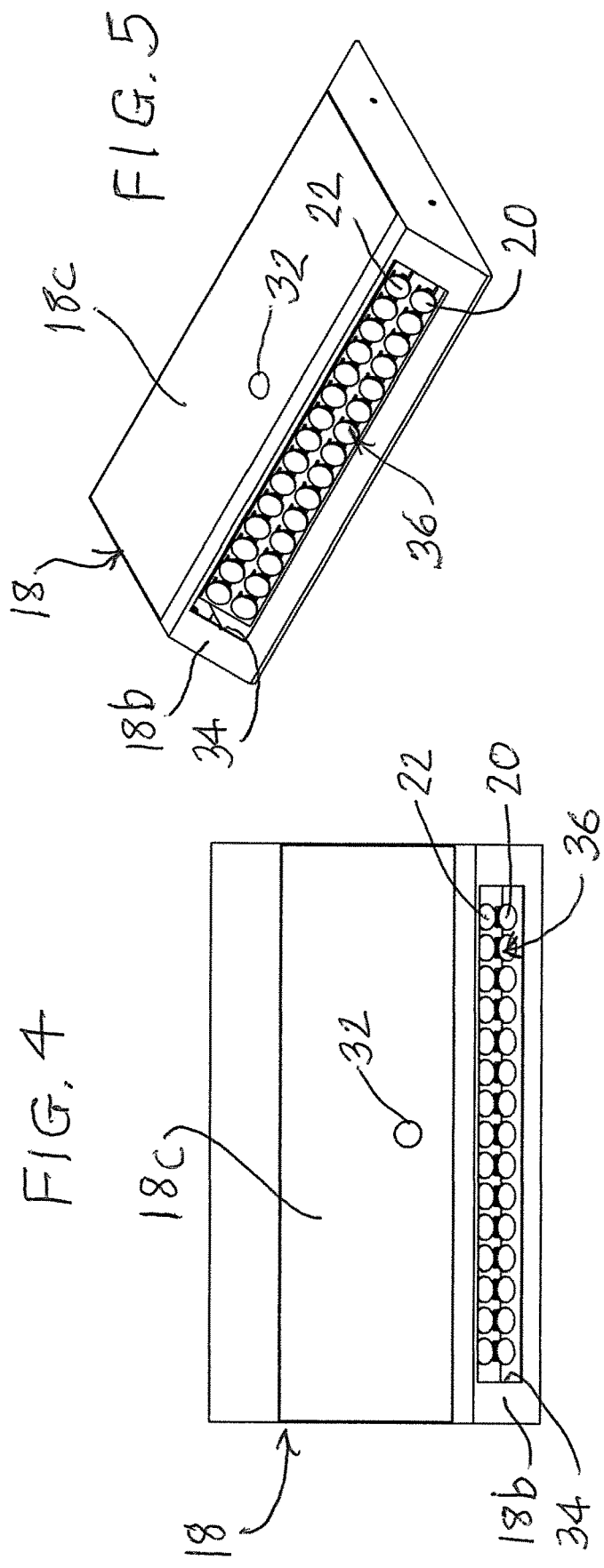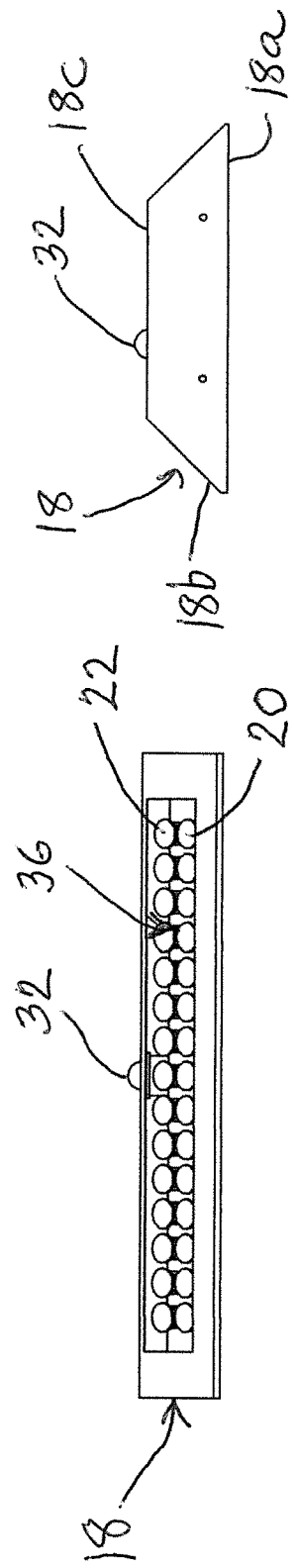

SYSTEM FOR NEUTRALIZING PATHOGENS ON TACTILE SURFACES

BACKGROUND OF THE INVENTION

1. Field of the Invention

The present invention generally relates to treatment apparatus for disinfecting surfaces and, more specifically, to a system for neutralizing pathogens on tactile surfaces.

2. Description of the Prior Art

The public is confronted on a daily basis with the numerous surfaces that need to be touched during normal uses, including vending machines, escalators, kiosks with interactive screens and automatic teller machines (ATMS) are only a few examples of items that are touched by an inordinate number of people that can harbor and transfer pathogens highly associated with illnesses and diseases. *E. coli, salmonella* and *Staphylococcus aureus* and, more recently, coronavirus Covid-19 that they can be found on commonly used surfaces that can easily spread to those in the general public through contact with the surfaces. If untreated, these bacteria and viruses can be transferred easily to cause serious illness and possibly death. The cleaning of cash dispensers and ATMs is provided by cleaning at defined periods (once every 2 weeks, once a month, once every 2 months). Generally, this cleaning does not provide 100% disinfection. And the cleaning is carried out using common detergents. Since these methods do not provide the required sterile medium, it threatens public health. The above mentioned reality in the research has also been proven in the laboratory. This physical cleaning causes extra costs for sector companies. For the reason of these costs, daily sterilization required cannot be provided by sector companies. Numerous approaches have been proposed for treating commonly-used surfaces to prevent the spreading of microbial and virus-based diseases. These include applying chemical disinfectants to the surfaces. For example, an automatic and electronic disinfection and sterilization system for ATM and cash dispensers is disclosed in WO 2016 1090828 that discloses a disinfection and sterilization system designed for use with ATMs and other surfaces. A nozzle spraying system is placed on ATMs and cash dispensers in the region (i.e. on the keypad and touch screen, etc.) that is desired to be cleaned by the spraying the solution coming from a solution reservoir by means of a suction-pushing pump and a pipe system. A nozzle spraying system protector-lid is the protector lid that is formed in order to prevent any intervention to the nozzle spraying system. Also providing sterilization and disinfection, is a UV light at a wave length used for sterilization of the surfaces of the ATM and cash dispenser.

An ATM surface cleaning device is disclosed and CN number 208552563. The device is a mobile device that can be fixed to or clamped on the outer side of an ATM machine body. A sliding mechanism is provided that includes vertically arranged sliding rails for sliding a sterilization device vertically upwardly and downwardly on the rails to sterilize the ATM at different positions on the outer surface of the ATM machine.

In published patent application US 20170080117 a system and method for inactivating pathogens using visible light and/or UV light are disclosed utilizing a first light source that emits light having a peak wavelength in the range of number 100 nm to 500 nm and a second light source that emits visible light. The light sources are can be independently controlled.

In published patent application US number 20180339075 devices are disclosed for surface treatment with ultraviolet light. The device utilizes one or more illuminators for generating ultraviolet radiation at a number of contact the surfaces. A control unit controls the ultraviolet radiation on the contact surfaces. The disinfection illuminators can be used by interactive devices used by the general public, including gas station pumps, doorknobs, keypads and other places having commonly-used surfaces that can be treated by the disinfection illuminators.

A problem common to many of the prior art devices is that they do not provide protection from protecting users from the UV light that can be received within and damage the retinas in a user's eyes.

SUMMARY OF THE INVENTION accordingly, it is an object of the invention to provide a system for neutralizing pathogens on a tactile surface arranged to be touched or contacted by a user's hands that does not have the disadvantages inherent in prior art devices it is another object of the invention to provide a system as in the previous object that is simple in construction and economical to manufacture.

It is still another object of the invention to provide a system as in the previous objects that can be used for disinfecting numerous surfaces normally or typically touched by many people, including, but not limited to, ATMs, cash dispensers, sliding handles on escalators, card filling stations and public areas, vending machines, hand drying machines in bathrooms, etc.

It is yet another object of the invention to provide a system of the type suggested above that includes both UV sources and white light sources controlled by a programmable controller programmed to normally maintain the UV sources energized except when a person is in proximity in which case the UV sources are de-energized and white light sources are energized until the person is no longer detected or for a program the time interval.

It is a further object of the invention to provide a system of the type under discussion that can be secured to an ATM machine.

It is still further object of the invention to provide a system as in the above objects that can be used to disinfect all patio surfaces on an ATM machine, including a keyboard, touchscreen, credit card reader etc.

It is yet a further object of the invention to provide a system as in the previous objects that includes a dedicated unit secured to an ATM, the unit including a housing with a programmable controller that can be easily and quickly accessed to either re-program the controller or replace UV or white light sources.

In order to achieve the above objects, as well as others that will become evident hereinafter, the system for neutralizing pathogens on a tactile surface comprises a housing and attachment means for attaching the housing to a support surface generally above the tactile surface. A UV light source is provided on the housing arranged above a surface to be irradiated this. Personnel detection means is provided for detecting the presence of a person in sufficient proximity to the tactile surface to touch or contact the tactile surface. Personnel detector is provided for detecting the presence of a person in sufficient proximity to the tactile surface to touch or contact the surface. Control means normally energizes the UV light source and de-energizes the UV light source upon detection of a user in sufficient proximity to allow the user to touch or contact the tactile surface at which time the tactile surface is illuminated by the white light source.

BRIEF DESCRIPTION OF THE DRAWINGS

The above and other aspects, features and advantages of the present invention will be more apparent from the following description when taken in conjunction with the accompanying drawings, in which:

FIG. 4 is a front elevation view of the device shown in FIGS. 1-3, showing additional details of the device;

FIG. 5 is a perspective view of the device shown in FIG. 4;

FIG. 6 is a bottom plan view of the device shown in FIGS. 4 and 5;

FIG. 7 is a side elevation view of the device shown in FIGS. 4-6; and

DETAILED DESCRIPTION

Figure 1:
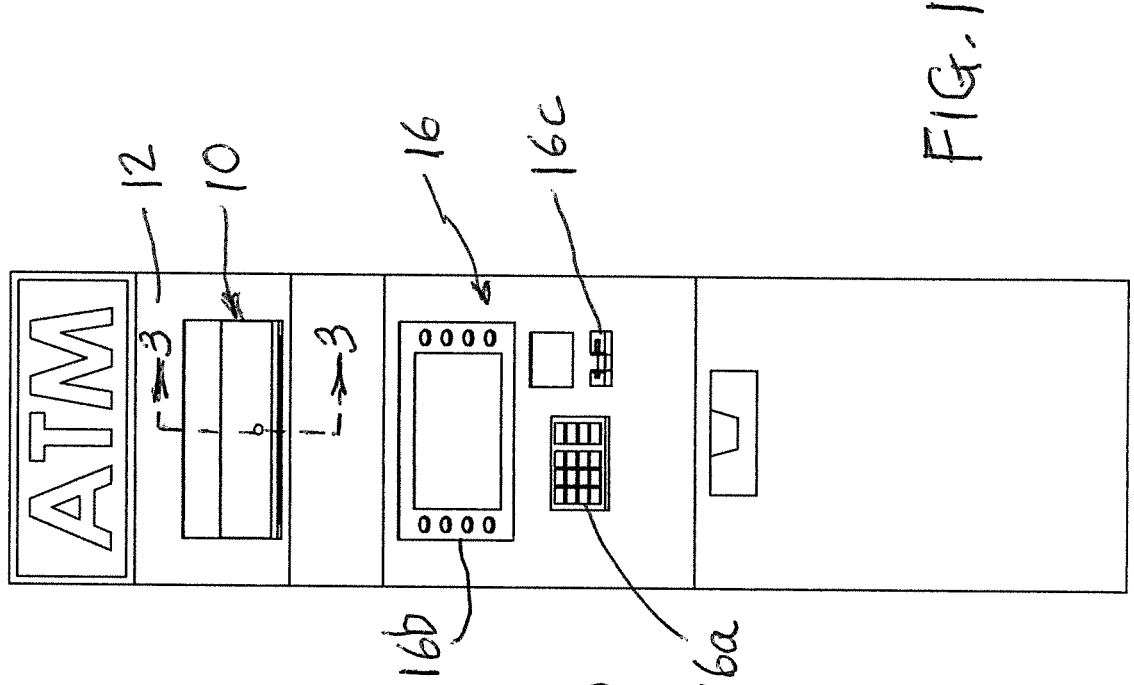
FIG. 1 is a front elevation view of an automatic teller machine (ATM) incorporating a system for neutralizing pathogens on tactile services in accordance with the invention.
Figure 2:
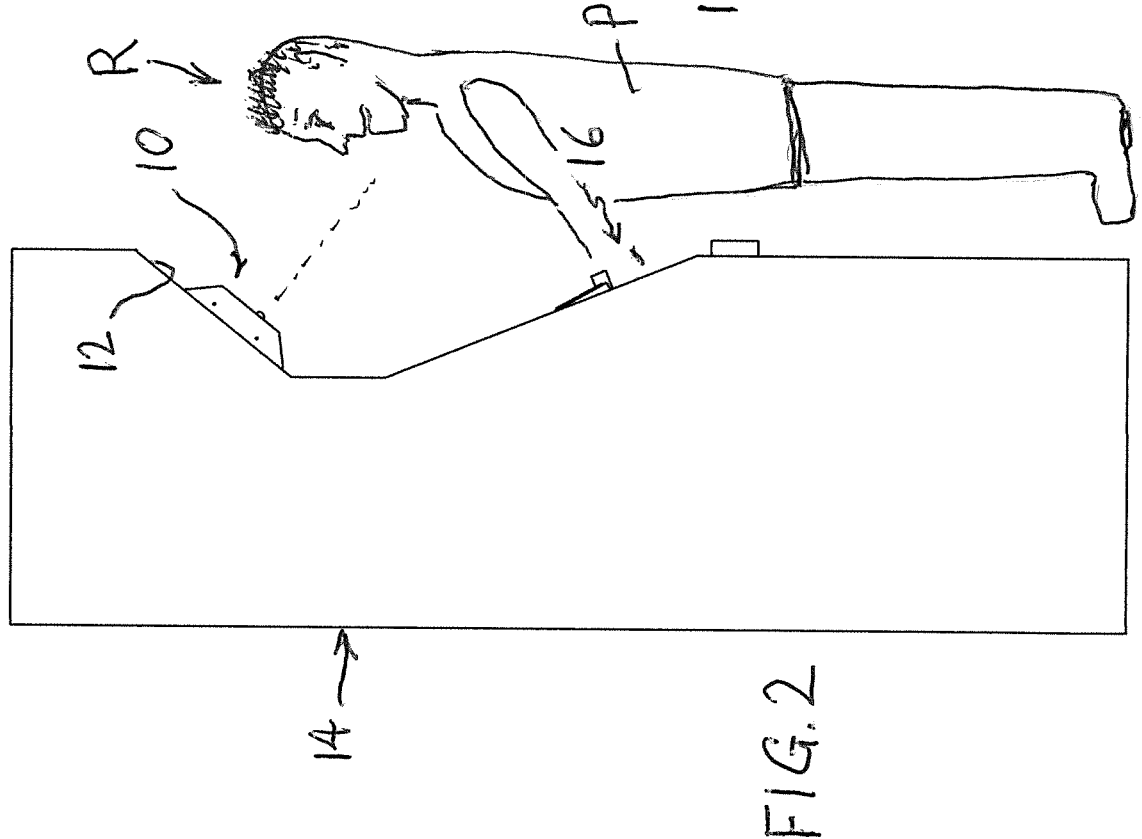
FIG. 2 is a side elevation view of the ATM shown in FIG. 1.

Referring now specifically to the Figures, in which identical or similar parts are designated by the same reference numerals throughout, and first referring to FIGS. 1 and 2, a device for neutralizing pathogens in accordance with the invention is generally designated by the reference number 10.

The device 10 is shown mounted on an inclined surface 12 of an automated teller machine (ATM) 14. The ATM 14 is typically provided with the tactile surfaces 16 that includes a keyboard 16a, a touch screen 16b and a credit card insertion port 16c. These tactile surfaces are typically touched or contacted numerous times during the course of a day by people that use the ATM to make deposits, make withdrawals or check account balances.

As shown in FIG. 2, the surface 12 on which the device 10 is mounted is inclined relative to the vertical direction by an angle θ. However, this will become evident hereinafter, the device 10 can be mounted on any surface in which the angle θ can be within the range of 0-90°.

FIG. 2 also indicates a region R in proximity to the ATM 14 in which a person or user P of the ATM generally stands while using the ATM. One of the features of the invention is that the device 10 generates two different types of light. The first is ultraviolet (UV) light to illuminate the tactile surface 16 as well as white light to illuminate and make more visible the tactile surface 16 to a person P during use of the ATM. Generally, only one of these sources of light is generated at any given time, as to be more fully described, as a function of the presence or absence of a user or person P within the region R. Thus, while there is no user in the region R the device 10 generates UV light to neutralize or disable pathogens on the tactile surface 16. However, as soon as a person P moves into the region R such user or person is detected and the transition is made from UV light to white light. White light continues to be generated as long as the person or user remains within the region R.

Figure 3:
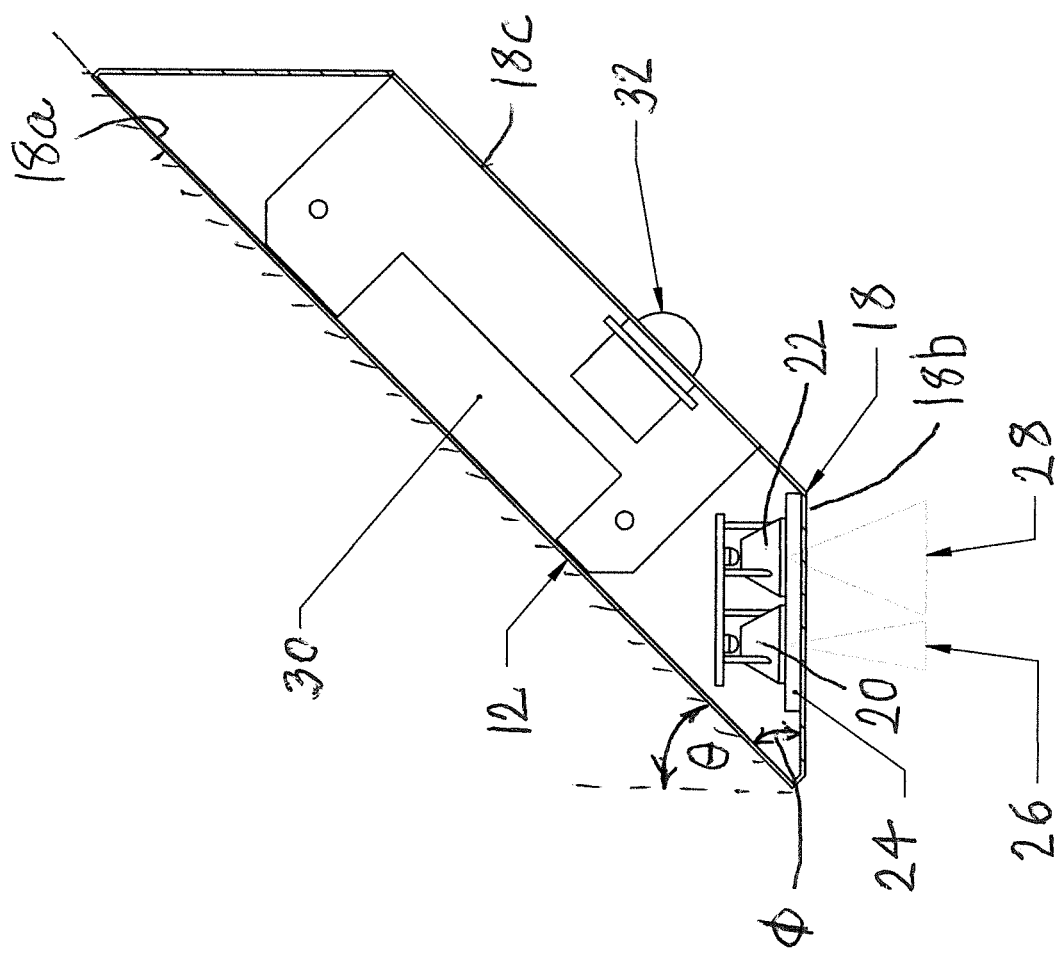
FIG. 3 is an enlarged cross-sectional view of the device taken along line 3-3 in FIG. 1.
Figure 9:
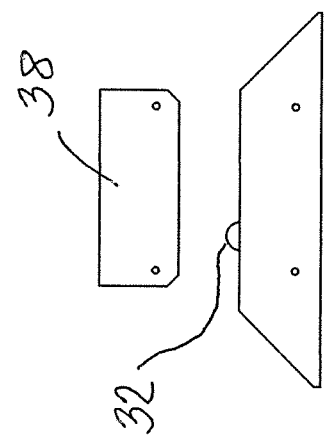
FIGS. 8-11 are similar to FIGS. 4-7, showing a cover panel partially removed to gain access to a programmable controller within the device.
Figure 11:
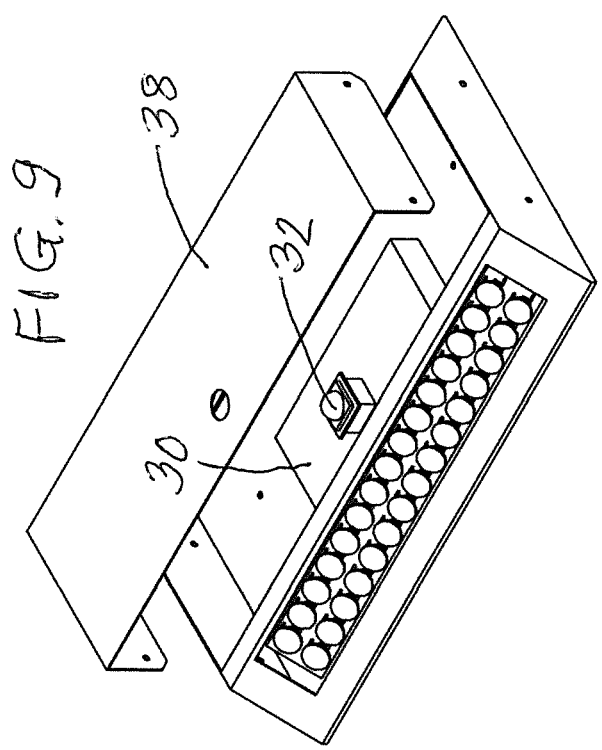
Figure 8:
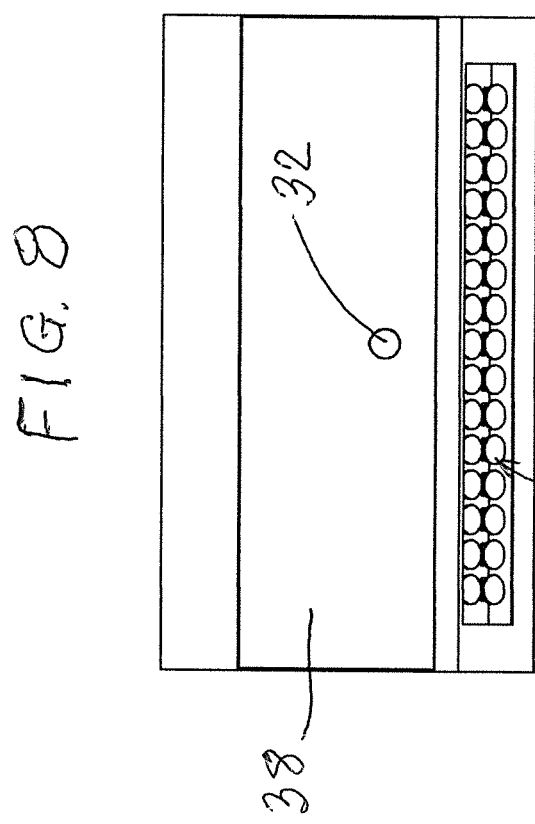
Figure 10:
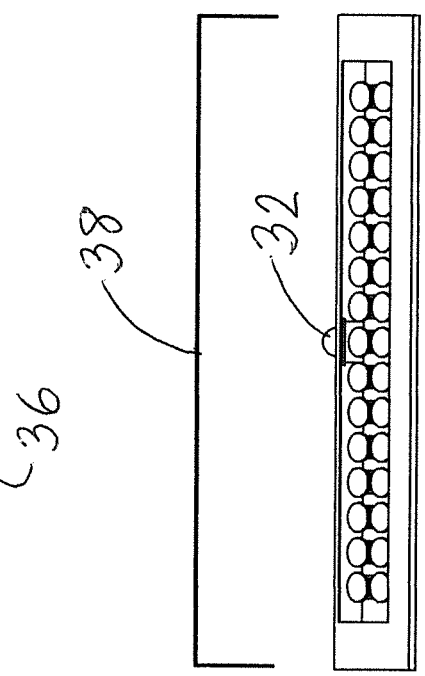

Referring to FIG. 3, the device 10 is shown mounted on the surface 12 inclined as aforementioned. Any suitable attachment means can be used for attaching the housing 18 to the support surface 12. The attachment means can be any suitable conventional means such as adhesive, mechanical fasteners or the like. The housing 18 has a rear or inner wall 18a attachable to the surface 12, and a lower generally horizontal wall 18b through which both forms of light emanate. A front or outer wall 18 C is generally parallel to the mounting wall 18 a. Mounted inside the housing 18 and in close proximity to the lower wall 18 b are the sources of UV light as well as white light. The UV light sources are designated by the number 20 while the white light sources are designated by the number 22. A protective lens 24 is positioned to protect the light sources 22, 24 while ensuring efficient transmission of the UV light. In a presently preferred embodiment, the light sources 20, 22 are advantageously LEDs for generating UV and white light, respectively. The LEDs as well as the protective lens 24 are selected to provide a generally narrow UV light beam 26 that has a radiation beam angle smaller than the white beam angle 28 of the generated white light beam. The more narrow UV light beam 26 focuses or concentrates the UV energy onto the tactile surface 16 to radiate greater energy in $\mu J/cm^2$ sufficient or adequate to neutralize or disable anticipated pathogens. The following table generally suggests some of the common pathogens and the energy levels required to kill them. The white light LEDs are selected to provide adequate illumination of the tactile surfaces so that a user can properly see them even under low light conditions.

As indicated, a feature of the invention is to disable the UV light source 24 whenever a user P enters the region R to prevent the user from being excessively exposed to UV light that they can create sunburn, eye injury or even skin cancer. To avoid such potential hazards, the device 10 is provided with a programmable controller with a sensor input and a timer circuit 30 contained within the housing 18. The controller 30 sensor input is connected to a passive infrared (PIR) sensor 32 selected to detect the presence of a person P within the region R. The programmable controller 30 normally energizes the UV source 20 but de-energizes the UV source as soon as the sensor 32 detects a person using the ATM. Substantially simultaneously with the de-energization of the UV sources 20 the white light source 22 is energized to illuminate the tactile surface 16 to facilitate data entry. In place of a PIR sensor the invention also contemplates the use of a microwave sensor to detect the presence of a person P within the region R. When a microwave sensor is used a microwave transmitter emits microwaves that radiate into the region R, a person P within that region reflecting microwaves that are then detected by the microwave sensor. The advantage of using microwaves is that they are more tamperproof and can effectively detect the presence of a person even of the sensor 32 is covered by paint or other blocking barriers placed between the sensor 32 and the region R.

The programmable controller 30 may also be provided with a timer circuit that regulates with the UV source 20 and the white light source 22 are energized and de-energized. The programmable controller can, for example, be programmed to de-energize a UV source 20 and maintain the source de-energized for a predetermined time. After the person P exits or leaves the region R as an added safety precaution to ensure that no UV is emitted as the person exits the region R.

Referring to FIGS. 4-7 the housing 18 shown provided with a rectangular opening 34 that extends substantially along the entire with of the housing 18 within the bottom wall 18 *b* the light sources 20, 22 are arranged in an array 36 to emit UV and white light, respectively, through the rectangular opening 34 either directly or through a UV transmissive protective lens 24. The array 36 of light sources is not critical and, for example, one role of light sources can be UV light sources while the other role are white light sources. The light sources can also alternate within the same row. Depending on the distance between the position of the device 10 in relation to the tactile surface 16 and the desired potency of the UV, it is possible to increase the number of UV light sources in relation to the number of white light sources, or vice versa. A person skilled in the art will know how to select and arrange if he had to different types of light sources to maximize the desired effects.

Referring to FIGS. 8-11, these are similar to FIGS. 4-7, but shown with a cover 38 of the housing 18 removed to show the interior of the housing and a means for providing access to the programmable controller 30 as well as the sensor 32. Removal of the cover 38 can also provide access to the light sources 20, 22 for removal or replacement.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A device for neutralizing pathogens on a tactile surface arranged to be touched or contacted by a user's hand, comprising a housing; attaching means for attaching the housing to a support surface generally above the tactile surface; a UV light source on the housing arranged to irradiate UV radiation on the tactile surface; a white light source on the housing arranged to irradiate white light on the tactile surface; personnel detection means for detecting the presence of a person in sufficient proximity to the tactile surface to touch or contact the tactile surface; control means for normally energizing the UV light source and de-energizing the UV light source and energizing said white light source upon detection of a user in sufficient proximity to allow a user to touch or contact the tactile surface.

2. A device as defined in claim 1, wherein the UV light source is generally above the tactile surface.

3. A device as defined in claim 2, wherein the UV radiation is directed substantially vertically downwardly.

4. A device as defined in claim 1, wherein the housing is mounted on a surface inclined at an angle $\theta$ relative to the vertical direction, and the housing has a generally horizontal wall through which the UV radiation is transmitted offset from the mounting surface an angle $\phi=90°-\theta$.

5. A device as defined in claim 1, wherein the UV light source emits UV-C radiation.

6. A device as defined in claim 1, further in combination with a tactile data interface.

7. A device as defined in claim 6, wherein the tactile data interface comprises a data entry keyboard.

8. A device as defined in claim 6, wherein the tactile data interface comprises a touch screen.

9. A device as defined in claim 1, wherein control means is a programmable controller for controlling the on and off times of the UV and white light sources.

10. A device is defined in claim 1, wherein a plurality of UV and white light sources are provided.

11. A device as defined in claim 10, wherein UV and white light sources are arranged in an array.

12. A device as defined in claim 11, wherein light sources are arranged into substantially parallel rows, a first role comprising a plurality of UV light sources and a second row comprising a plurality of white light sources.

13. A device as defined in claim 1, wherein said UV light sources have am angles smaller than beam angles emitted by white light sources.

14. A device is defined in claim 1, wherein said light sources comprise UV LEDs.

15. A device as defined in claim 14, wherein the UV LEDs are UV-C LEDs.

16. A device as defined in claim 1, wherein said white light sources comprise white light LEDs.

17. A device as defined in claim 1, wherein the device is mounted on a surface of an ATM.

18. A device as defined in claim 17, wherein the ATM tactile surface comprises at least one of a keyboard, touch-screen and a credit card reader.

* * * * *